United States Patent
Shoji et al.

(10) Patent No.: US 9,717,516 B2
(45) Date of Patent: Aug. 1, 2017

(54) ENDOSCOPE TREATMENT TOOL

(71) Applicant: OLYMPUS CORPORATION, Tokyo (JP)

(72) Inventors: Keita Shoji, Hamburg (DE); Masatoshi Sato, Tokyo (JP); Keita Suzuki, Chino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/746,203

(22) Filed: Jun. 22, 2015

(65) Prior Publication Data

US 2015/0282826 A1    Oct. 8, 2015

Related U.S. Application Data

(63) Continuation of application No. PCT/JP2014/063052, filed on May 16, 2014.

(30) Foreign Application Priority Data

May 17, 2013   (JP) ................................. 2013-105605

(51) Int. Cl.
*A61B 17/00* (2006.01)
*A61B 17/29* (2006.01)
(Continued)

(52) U.S. Cl.
CPC .............. *A61B 17/29* (2013.01); *A61B 10/04* (2013.01); *A61B 10/06* (2013.01);
(Continued)

(58) Field of Classification Search
CPC ..... A61B 10/04; A61B 10/06; A61B 10/0233; A61B 10/0241; A61B 10/025;
(Continued)

(56) References Cited

U.S. PATENT DOCUMENTS

| | | | | |
|---|---|---|---|---|
| 5,649,955 A | * | 7/1997 | Hashimoto | A61B 17/29 600/562 |
| 5,947,996 A | * | 9/1999 | Logeman | A61B 17/29 600/564 |
| 2008/0195144 A1 | | 8/2008 | Hashimoto | |

FOREIGN PATENT DOCUMENTS

| | | |
|---|---|---|
| EP | 2474273 A1 | 7/2012 |
| JP | 4056989 B2 | 3/2008 |

(Continued)

OTHER PUBLICATIONS

Jul. 8, 2014 International Search Report issued in International Application No. PCT/JP2014/063052.

(Continued)

*Primary Examiner* — Katherine M Shi
*Assistant Examiner* — Mohamed Gabr
(74) *Attorney, Agent, or Firm* — Oliff PLC

(57) ABSTRACT

An endoscope treatment tool includes a sheath; a support part; a pair of forceps members that are arranged in front of the sheath and are supported so as to be relatively rotatable around a rotation shaft provided at the support part; a linear member that is inserted through the sheath so as to be capable of advancing into and retracting from the sheath, brings opposed surfaces, which are respectively provided closer to distal end sides of the pair of forceps members than the rotation shaft, closer to each other as the linear member is separated from the rotation shaft, and separates the pair of opposed surfaces from each other as the linear member approaches the rotation shaft; an elastic member that is supported by the linear member or the support part; and a locking portion that is provided on the linear member or the forceps members.

2 Claims, 8 Drawing Sheets

(51) Int. Cl.
*A61B 10/06* (2006.01)
*A61B 10/04* (2006.01)
*A61B 90/00* (2016.01)

(52) U.S. Cl.
CPC *A61B 17/00234* (2013.01); *A61B 2017/0034* (2013.01); *A61B 2017/00296* (2013.01); *A61B 2017/2926* (2013.01); *A61B 2017/2939* (2013.01); *A61B 2090/034* (2016.02); *A61B 2090/08021* (2016.02)

(58) Field of Classification Search
CPC ............ A61B 10/0266; A61B 10/0275; A61B 17/00234; A61B 17/29; A61B 17/282; A61B 17/2816; A61B 17/2833; A61B 17/32; A61B 17/3201; A61B 2017/00296; A61B 2017/0034; A61B 2017/2926; A61B 2017/2939; A61B 2017/2845; A61B 2017/2911; A61B 2017/2912; A61B 2017/2932; A61B 2017/2922; A61B 2090/034; A61B 2090/08021; A61B 90/03; A61B 18/1445
USPC .......................................................... 606/205
See application file for complete search history.

(56) References Cited

FOREIGN PATENT DOCUMENTS

| | | |
|---|---|---|
| JP | 4197983 B2 | 12/2008 |
| WO | 2007018264 A1 | 2/2007 |
| WO | 2012002091 A1 | 1/2012 |
| WO | 2013/140648 A1 | 9/2013 |

OTHER PUBLICATIONS

Dec. 15, 2016 European Search Report issued in Patent Application No. 14797258.2.

\* cited by examiner

ENDOSCOPE TREATMENT TOOL

This application is a continuation application based on PCT/JP2014/063052, filed on May 16, 2014 and claiming priority based on Japanese Patent Application No. 2013-105605, filed in Japan on May 17, 2013. The contents of both the Japanese Patent Application and the PCT Application are incorporated herein by reference.

TECHNICAL FIELD

The present invention relates to an endoscope treatment tool used after being endoscopically inserted into a body cavity.

BACKGROUND ART

In the related art, endoscope treatment tools (hereinafter also simply referred to as "treatment tools") used to perform various kinds of treatment on tissue within a body cavity after being endoscopically inserted into the body cavity have been studied. As an example of the treatment tools, a treatment tool described in Japanese Patent No. 4197983 and Japanese Patent No. 4056989 is known.

A distal end of this treatment tool is provided with a pair of forceps members that are relatively rotatably supported around a rotation shaft.

The rotation shaft is attached to a distal end portion of a longitudinal sheath, and an operating wire is inserted through the sheath so as to be capable of advancing into and retracting from the sheath. An operating section is connected to proximal ends of the sheath and the operating wire. Link members are respectively attached to proximal ends of the pair of forceps members. Proximal ends of these link members are rotatably connected to a distal end of the operating wire.

The pair of forceps members are relatively rotated around the rotation shaft by operating the operating section to advance and retract the operating wire with respect to the sheath. In this way, switching is made between a closed state where the pair of forceps members abut against each other and a fully open state where the pair of forceps members are separated from each other.

SUMMARY OF THE INVENTION

Solution to Problem

An endoscope treatment tool related to a first aspect of the present invention includes a sheath; a support part that is attached to a distal end portion of the sheath; forceps members that are arranged in front of the sheath, are supported so as to be relatively rotatable around a rotation shaft provided at the support part, and have a pair of opposed surfaces; a linear member that is inserted through the sheath so as to be capable of advancing into and retracting from the sheath, brings the pair of opposed surfaces, which are provided closer to a distal end side than the rotation shaft, closer to each other as the linear member is separated from the rotation shaft, and separates the pair of opposed surfaces from each other as the linear member approaches the rotation shaft; an elastic member that is supported by the linear member or the support part; and a locking portion that is provided on the linear member or the forceps members. The locking portion is separated from the elastic member in a natural state when the linear member moves so as to be separated from the rotation shaft and the pair of the opposed surfaces abut against each other. The locking portion moves to a contact position where the locking portion comes into contact with the elastic member in the natural state when the linear member moves so as to approach the rotation shaft and the pair of the opposed surfaces are separated from each other. As the locking portion is further moved such that the locking portion moved to the contact position approaches the rotation shaft, the elastic member is elastically deformed, and the pair of opposed surfaces are further separated from each other than when the locking portion is located at the contact position.

According to the endoscope treatment tool related to a second aspect of the present invention based on the first aspect, the elastic member may be a coil spring in which an element wire is spirally wound and the element wires adjacent to each other are separated from each other in an axis direction of the spiral in the natural state, the coil spring may be supported such that the linear member is inserted through the coil spring substantially parallel to the axis direction of the spiral, and the locking portion may be provided closer to a proximal end side of the linear member than the coil spring, the support part may have a support surface that supports the coil spring at a position closer to the distal end side than the coil spring, and the coil spring may be compressed in a longitudinal direction of the sheath by the locking portion and the support surface when the linear member is moved so as to approach the rotation shaft.

According to the endoscope treatment tool related to a third aspect of the present invention based on the second aspect, the linear member may be movable so as to approach the rotation shaft up to a position where the coil spring is elastically compressed and the element wires adjacent to each other in the axis direction abut against each other.

According to the endoscope treatment tool related to a fourth aspect of the present invention based on the first aspect, the elastic member may be a plate spring that is arranged such that a thickness direction of the elastic member becomes parallel to a longitudinal direction of the sheath and that is bent so as to become convex in any one direction in the longitudinal directions in its natural state, the plate spring is formed with a through-hole passing therethrough in the thickness direction, the linear member may be inserted through and supported by the through-hole of the plate spring, the locking portion may be provided closer on the proximal end side of the linear member than the plate spring, the support part may have a support surface that supports the plate spring, at a position closer to the distal end side than the plate spring, and the plate spring may be brought close to a flat shape by the locking portion and the support surface when the linear member is moved so as to approach the rotation shaft.

According to the endoscope treatment tool related to a fifth aspect of the present invention based on the fourth aspect, the linear member may be movable so as to approach the rotation shaft until the plate spring is deformed into a flat shape.

According to the endoscope treatment tool related to a sixth aspect of the present invention based on the first aspect, the elastic member may be formed in a tubular shape and is externally fitted to the support part and thereby supported by the support part, and the locking portion may be provided on at least one of the forceps portions, and the locking portion may deform the elastic member when the linear member is moved so as to approach the rotation shaft.

According to the endoscope treatment tool related to a seventh aspect of the present invention based on the sixth aspect, the locking portion is provided at a proximal end of the forceps member.

DESCRIPTION OF EMBODIMENTS

First Embodiment

A first embodiment of an endoscope treatment tool related to the present invention will be described below, referring to FIGS. 1 to 3. A case where the endoscope treatment tool is gripping forceps will be described below as an example.

Figure 1:
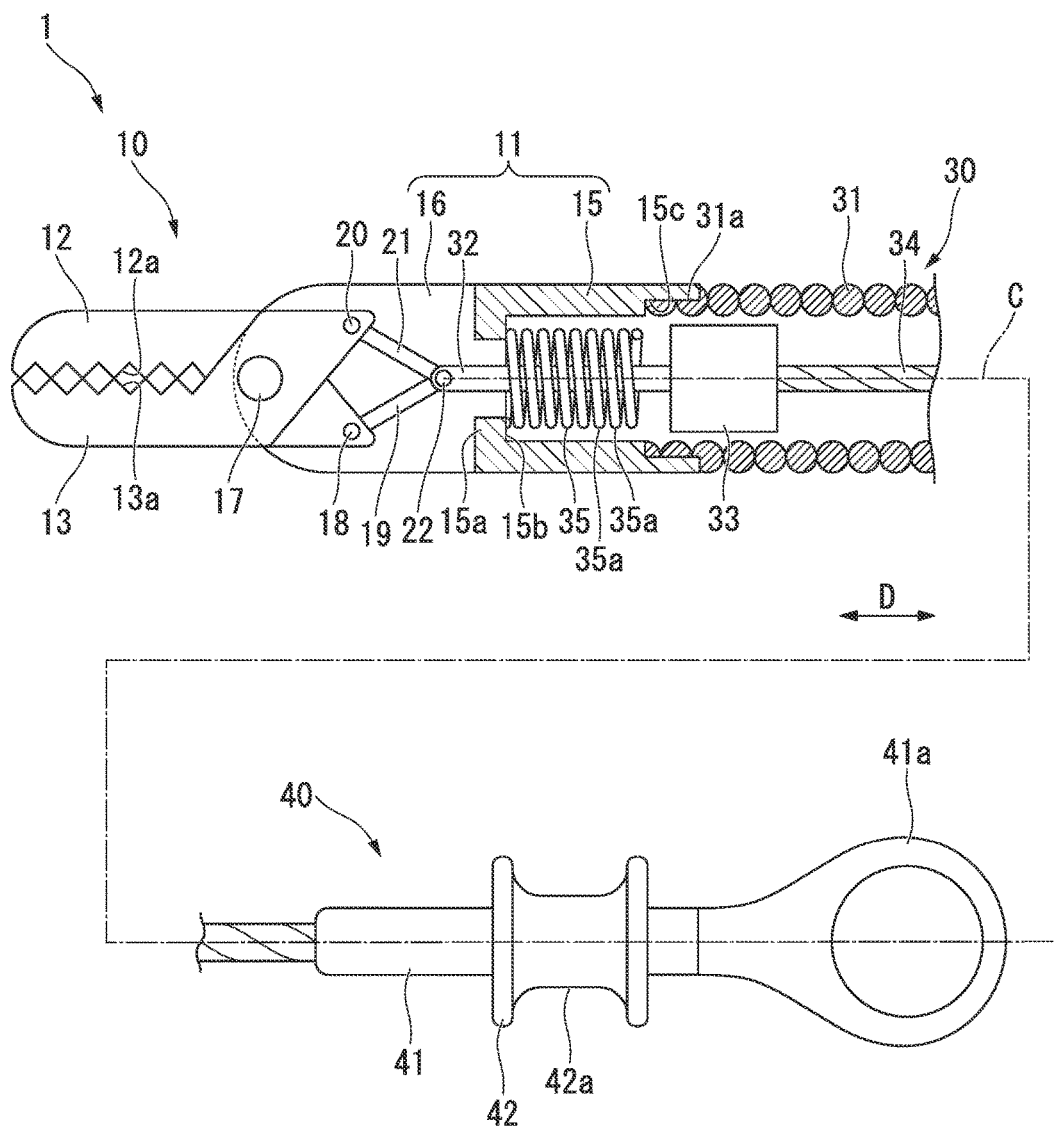
FIG. 1 is a partial fragmentary view of a side surface in a first usage pattern of gripping forceps of a first embodiment of the present invention.
Figure 2:
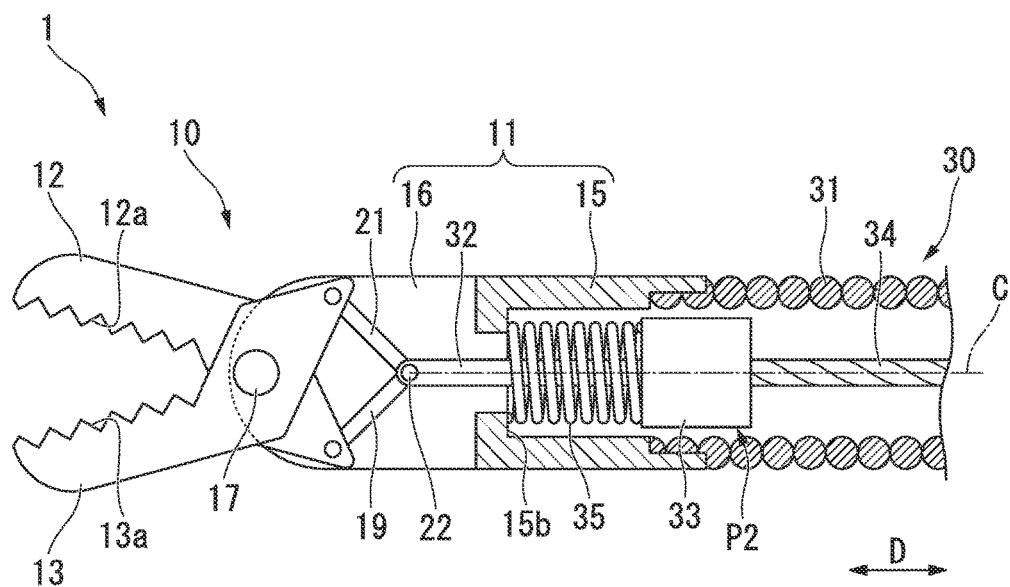
FIG. 2 is a cross-sectional view of the side surface on a distal end side in a second usage pattern of the gripping forceps.

As shown in FIG. 1, the gripping forceps 1 include a gripping section 10 that grips tissue, an insertion section 30 that is provided on a proximal end side of the gripping section 10 and has flexibility, and an operating section 40 that is provided on the proximal end side of the insertion section 30 and operates the gripping section 10.

In FIG. 1, blade surfaces 12a and 13a to be described below illustrate a first usage pattern of the gripping forceps 1 brought into a closed state.

The gripping section 10 includes a distal end cover member (support part) 11 and a pair of forceps members 12 and 13 rotatably supported by the distal end cover member 11.

The distal end cover member 11 has a cylindrical part 15 that forms a cylindrical shape of which an axis C extends back and forth, and a pair of covers 16 that extend so as to sandwich the axis C from a distal end surface of the cylindrical part 15 (one of the pair of covers 16 is shown).

A distal end portion of the cylindrical part 15 is provided with an annular member 15a that protrudes from an inner peripheral surface of the cylindrical part. The surface of the annular member 15a on the proximal end side is a support surface 15b. A stepped portion 15c of which the internal diameter is set to be greater than that of the other portions of the cylindrical part 15 is formed inside at a proximal end of the cylindrical part 15.

Distal end portions of the pair of covers 16 are provided with a rotation shaft 17 that joins the covers 16 together.

In a side view, the forceps members 12 and 13 are arranged so as to intersect each other at a central portion thereof in an extending direction, and are each relatively rotatably supported around the above-mentioned rotation shaft 17 at this central portion. In this example, the blade surfaces (opposed surfaces) 12a and 13a that face each other and have minute concave portions and convex portions formed therein are provided closer to the distal end sides of the forceps members 12 and 13 than the rotation shaft 17.

The forceps members 12 and 13 are arranged between the pair of covers 16. The distal end cover member 11 and the forceps members 12 and 13 are formed from metal, such as stainless steel, which has biocompatibility.

A distal end of the link member 19 is rotatably coupled to a proximal end of the forceps member 12 via a link rotation shaft 18. Similarly, a distal end of the link member 21 is rotatably coupled to a proximal end of the forceps member 13 via a link rotation shaft 20. A proximal end of the link member 19 and a proximal end of the link member 21 are rotatably coupled together by a common rotation shaft 22. The common rotation shaft 22 is arranged on an axis C.

The forceps members 12 and 13, the link members 19 and 21, and the rotation shafts 18, 20, and 22, which are configured in this way, constitute a well-known pantagraph type link mechanism. That is, the forceps members 12 and 13 rotate around the rotation shaft 17 when the common rotation shaft 22 moves to the proximal end side and is separated from the rotation shaft 17, and thereby, the anti-slip surfaces 12a and 13a approach each other and are brought into the closed state where the opening angle of the anti-slip surfaces 12a and 13a is 0. On the other hand, as the common rotation shaft 22 moves to the distal end side and approaches the rotation shaft 17, the anti-slip surfaces 12a and 13a are separated from each other, and are brought into a fully open state where the opening angle is the greatest. The opening angle of the anti-slip surfaces 12a and 13a can be increased until the common rotation shaft 22 moves to the distal end side and a coil spring 35 (to be described below) is brought into a densely wound state.

The insertion section 30 has a sheath 31, a wire connector 32 that is inserted through the cylindrical part 15 and the sheath 31 in a state where a distal end thereof is connected to the common rotation shaft 22, a stopper (locking portion) 33 that is attached to a proximal end of the wire connector 32, an operating wire 34 that is attached to a proximal end of the stopper 33, and a coil spring (elastic member) 35 that has a distal end attached to the support surface 15b in a state where the spring is inserted through the wire connector 32.

In addition, the wire connector 32 and the operating wire (lineal member) 34 constitute a linear member.

A coiled sheath, which is wound in a densely wound manner in a longitudinal direction D of the sheath 31 parallel to the axis C of the sheath 31, is used as the sheath 31. The sheath 31 has flexibility, and has compressive resistance in the longitudinal direction D.

An outer peripheral surface of a distal end of the sheath 31 is formed with a stepped portion 31*a*. The sheath 31 is attached to a proximal end portion of the distal end cover member 11 by performing laser welding of the stepped portion 31*a* and the stepped portion 15*c* in a state where the stepped portion 31*a* of the sheath 31 and the stepped portion 15*c* of the distal end cover member 11 are engaged with each other.

By attaching the distal end cover member 11 and the sheath 31 in this way, the external diameter of the distal end cover member 11 and the external diameter of the sheath 31 can be made equal to each other, and the insertability of the gripping section 10 and the insertion section 30 can be enhanced.

The outer peripheral surface of the sheath 31 may be provided with a covering tube with frictional resistance.

The external diameter of the wire connector 32 is set to be smaller than the internal diameter of the annular member 15*a*.

The stopper 33 is formed in a substantially columnar shape from stainless steel or the like, and is arranged such that the axis of the stopper 33 becomes parallel to the longitudinal direction D. The external diameter of the stopper 33 is set to be smaller than the internal diameter of the cylindrical part 15 and the internal diameter of the sheath 31.

The operating wire 34 is inserted so as to be capable of advancing into and retracting from the sheath 31, and a proximal end side of the operating wire 34 extends up to the operating section 40.

The coil spring 35 is formed such that an element wire 35*a* of the coil spring 35 is spirally wound, and adjacent element wires 35*a* are separated from each other in an axis direction of a spiral in the natural state where no external forces other than gravity. The internal diameter of the coil spring 35 is set to be greater than the external diameter of the stopper 33.

The coil spring 35 is arranged within the cylindrical part 15. The coil spring 35 is supported by the distal end cover member 11 by being attached to the support surface 15*b* of the distal end cover member 11 in a state where the wire connector 32 is inserted through the coil spring 35 substantially parallel to the axis direction of the spiral.

As shown in FIG. 1, in the first usage pattern in which the anti-slip surfaces 12*a* and 13*a* abut against each other and are brought into the closed state, the wire connector 32 moves to the proximal end side together with the common rotation shaft 22. In this case, the stopper 33 is arranged at a separated position where the stopper is separated from the coil spring 35, and the coil spring 35 is in the natural state.

The operating section 40 has an operating section body 41 that is connected to a proximal end portion of the sheath 31, and a slider 42 that is provided on an outer peripheral surface of the operating section body 41 so as to be capable of advancing thereinto and retracting therefrom.

The operating section body 41 is formed in a substantially tubular shape, and an outer surface of the operating section body 41 is formed with a slit (not shown) that communicates with a conduit of the operating section body 41. A proximal end portion of the operating section body 41 is provided with a finger hooking ring 41*a*.

A concave portion 42*a* is formed in a side surface of the slider 42 over its whole circumference in a circumferential direction.

The slider 42 is attached to a proximal end portion of the operating wire 34 through the aforementioned slit of the operating section body 41.

Next, the operation of the gripping forceps 1 configured as described above will be described.

First, a case where the gripping section 10 and the insertion section 30 of the gripping forceps 1 of the present embodiment are inserted into a living body or the like, and the gripping forceps 1 are used in an environment, such as the inside of an esophagus, in which there is relatively no margin for surrounding space will be described.

A surgeon supports the gripping forceps 1 by inserting his/her thumb through the finger hooking ring 41*a* of the gripping forceps 1 in the first usage pattern and hooking his/her index finger and middle finger to the concave portion of the slider 42. The gripping section 10 is inserted into a living body. If the gripping section 10 reaches the vicinity of tissue to be treated, the slider 42 is pushed into the operating section body 41. Accordingly, as shown in FIG. 2, in a process in which the common rotation shaft 22 moves to the distal end side together with the operating wire 34 and the wire connector 32 and the anti-slip surfaces 12*a* and 13*a* are separated from each other, the stopper 33 moves to a contact position P2 where the stopper comes into contact with a proximal end of the coil spring 35 in the natural state and is locked to the coil spring 35.

In this case, the anti-slip surfaces 12*a* and 13*a* are bought into a state where the anti-slip surfaces are not separated from each other completely, in other words, a half-open state where the opening angle is between the closed state and the fully open state, and the gripping forceps 1 are brought into a second usage pattern.

If the slider 42 is further pushed in the gripping forceps 1 brought into the second usage pattern, the coil spring 35 in the natural state is compressed. Therefore, a force required to push the slider 42 increases as the slider is pushed to the distal end side. For this reason, the surgeon that operates the slider 42 can easily recognize whether or not the gripping forceps 1 are in the second usage pattern.

Additionally, since the position of the proximal end of the coil spring 35 in the natural state is constant with respect to the distal end cover member 11, the opening angle of the anti-slip surfaces 12*a* and 13*a* brought into the half-open state also has a constant value.

The anti-slip surfaces 12*a* and 13*a* of the gripping forceps 1 brought into the second usage pattern are made to abut against the tissue. The gripping forceps 1 are returned from the second usage pattern to the first usage pattern by pulling the slider 42 back to the operating section body 41, the tissue is gripped between the forceps members 12 and 13, and suitable treatment is performed.

Next, a case where the gripping forceps 1 are used in an environment where there is a relative margin for surrounding space.

Figure 3:
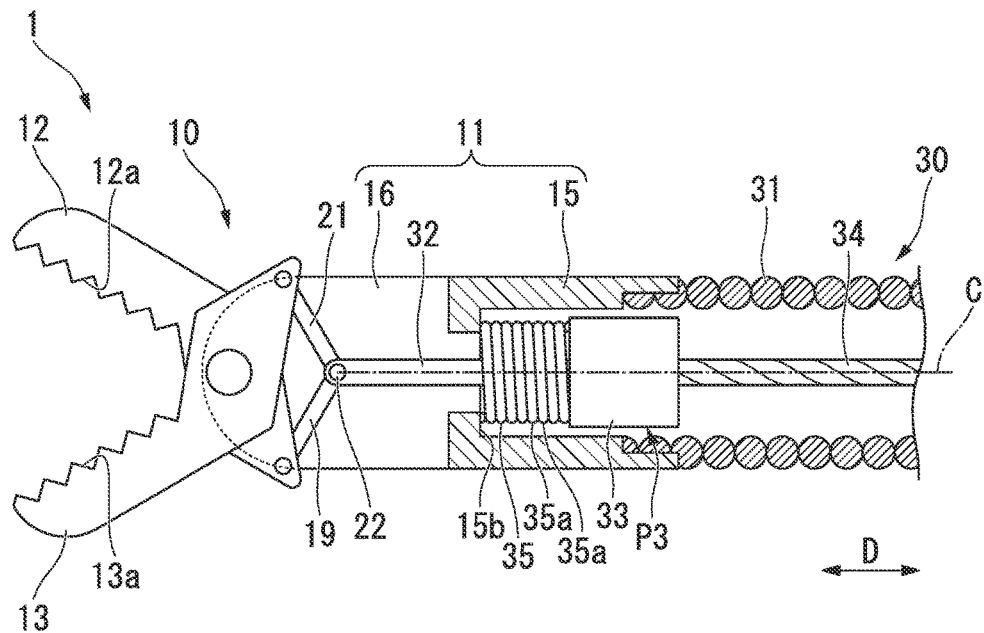
FIG. 3 is a cross-sectional view of the side surface on the distal end side in a third usage pattern of the gripping forceps.

In this case, if a slider 42 is further pushed in the gripping forceps 1 brought into the above-mentioned second usage pattern, the stopper 33 further moves to the distal end side and moves to a compression position P3 as shown in FIG. 3 from the contact position P2, and the coil spring 35 is elastically compressed in the longitudinal direction D by the stopper 33 and the support surface 15*b*.

In this case, as the common rotation shaft 22 moves to the distal end side together with the operating wire 34, the opening angle of the anti-slip surfaces 12*a* and 13*a* becomes larger than when the stopper 33 is at the contact position P2.

If the coil spring 35 is compressed up to a position where adjacent element wires 35*a* in the longitudinal direction D abut against each other, that is, until the coil spring is brought into the so-called densely wound state, the coil spring 35 cannot be compressed any further. The anti-slip surfaces 12a and 13a in this case are brought into the fully open state where the opening angle is the largest, and the gripping forceps 1 are brought into a third usage pattern.

The anti-slip surfaces 12a and 13a of the gripping forceps 1 brought into the third usage pattern are made to abut against the tissue. The gripping forceps 1 are returned from the third usage pattern to the first usage pattern by pulling the slider 42 back, the tissue is gripped between the forceps members 12 and 13, and suitable treatment is performed.

As described above, according to the gripping forceps 1 of the present embodiment, the anti-slip surfaces 12a and 13a are brought into the closed state, and the stopper 33 pushes the slider 42 from the first usage pattern arranged at the separated position where the stopper is separated from the coil spring 35 in the natural state. Accordingly, when the stopper 33 moves to the contact position P2 where the stopper comes into contact with the coil spring 35 in the natural state, the anti-slip surfaces 12a and 13a are brought into a half-open state. If the slider 42 is further pushed, the stopper 33 elastically deforms the coil spring 35, and the anti-slip surfaces 12a and 13a are brought into the fully open state.

Since the contact position P2 where the stopper 33 comes into contact with the coil spring 35 in the natural state becomes constant, the opening angle of the anti-slip surfaces 12a and 13a in the half-open state can be made constant.

By using the coil spring 35 through which the wire connector 32 is inserted as an elastic member, a force required to push the slider 42 while the stopper 33 moves from the contact position P2 to a compression position increases substantially in proportion to the displacement from the contact position P2 of the stopper 33 to the distal end side. For this reason, the surgeon that operates the slider 42 can easily recognize the position of the stopper 33 arranged between the contact position P2 and the compression position.

Moreover, since the coil spring 35 compressed until the coil spring is brought into the densely wound state cannot be compressed any further, the surgeon can easily recognize that the anti-slip surfaces 12a and 13a are in the fully open state.

Since the position of the proximal end of the coil spring 35 when being brought into the densely wound state becomes constant, the opening angle of the anti-slip surfaces 12a and 13a brought into the fully open state can be made constant.

The coil spring 35 is arranged inside the distal end cover member 11, that is, on the distal end side of the gripping forceps 1. Accordingly, when the slider 42 is pushed and is brought into the second usage pattern and the third usage pattern, the sheath 31, the operating wire 34, or the like can be extended to keep the opening angle of the anti-slip surfaces 12a and 13a from changing.

The present embodiment is configured such that a distal end of the coil spring 35 is attached to the support surface 15b. However, the distal end of the coil spring 35 may not be attached to the support surface 15b, and the wire connector 32 may only be inserted through the coil spring 35. This is because, even if such a configuration is adopted, the coil spring 35 can be supported by the wire connector 32. However, the position of the coil spring 35 can be further stabilized by attaching the distal end of the coil spring 35 to the support surface 15b.

Second Embodiment

Next, although a second embodiment of the present invention will be described referring to FIGS. 4 to 6, the same parts as the above embodiment will be designated by the same reference numerals and the description thereof will be omitted, and only different points will be described.

Figure 4:
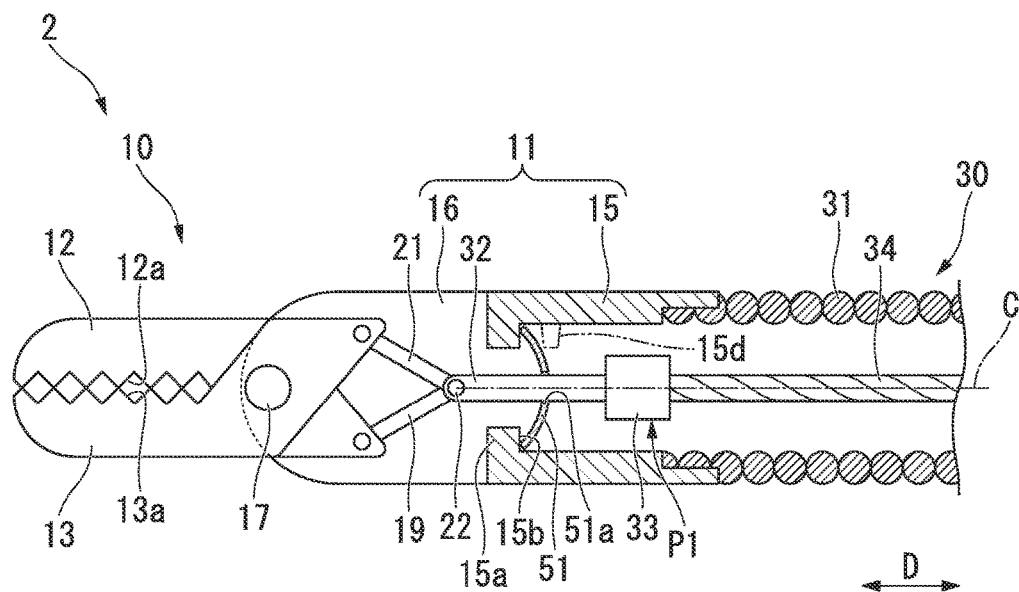
FIG. 4 is a cross-sectional view of the side surface on the distal end side in the first usage pattern of gripping forceps of a second embodiment of the present invention.

As shown in FIG. 4, gripping forceps 2 of the present embodiment include a plate spring (elastic member) 51 instead of the coil spring 35 of the gripping forceps 1 of the first embodiment.

The plate spring 51 is formed from stainless steel, resin, or the like in a shape such that the plate spring is bent so as to become convex toward one of thickness directions in a natural state. The plate spring 51 is formed with a through-hole 51a passing therethrough in its own thickness direction. The plate spring 51 is arranged within the cylindrical part 15 such that its own thickness direction becomes parallel to the longitudinal direction D. The plate spring 51 is supported by the wire connector 32 as the wire connector 32 is inserted through the through-hole 51a.

The external diameter of the plate spring 51 in the natural state is set to be greater than the internal diameter of the annular member 15a of the distal end cover member 11, and the internal diameter of the through-hole 51a is set to be smaller than the external diameter of the stopper 33.

In the present embodiment, the plate spring 51 is not attached to the support surface 15b and is arranged between the support surface 15b and the stopper 33.

It is more preferable that a protruding piece 15d that protrudes from the inner peripheral surface of the cylindrical part 15 is provided closer to the proximal end side than the plate spring 51 within the cylindrical part 15. By adopting such a configuration, movement of the plate spring 51 to the proximal end side is regulated, and the position of the plate spring 51 within the cylindrical part 15 can be stabilized.

In the gripping forceps 2 configured in this way, the stopper 33 is arranged at the separated position P1 where the stopper is separated from the plate spring 51 in the first usage pattern in which the anti-slip surfaces 12a and 13a are brought into the closed state.

Figure 5:
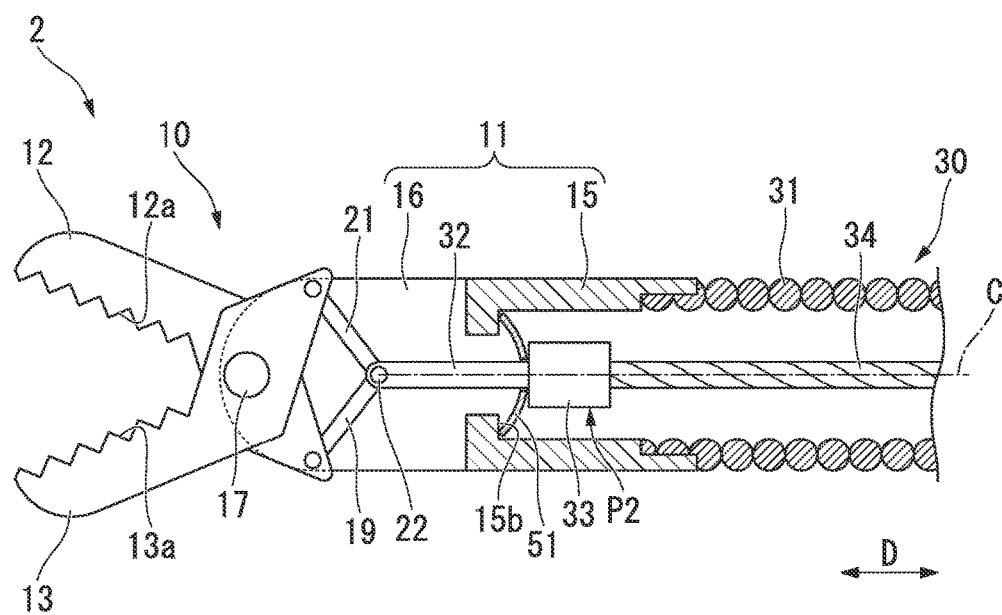
FIG. 5 is a cross-sectional view of the side surface on the distal end side in the second usage pattern of the gripping forceps.

Then, by pushing the slider 42, as shown in FIG. 5 the stopper 33 moves to the contact position P2 where the stopper comes into contact with a proximal end of the plate spring 51 in the natural state. In this case, the anti-slip surfaces 12a and 13a are brought into the half-open state where the anti-slip surfaces are separated from each other by a certain distance, and the gripping forceps 2 are brought into the second usage pattern. Since the position of the proximal end of the plate spring 51 in the natural state becomes constant with respect to the distal end cover member 11, the opening angle of the anti-slip surfaces 12a and 13a brought into the half-open state also has a constant value.

Figure 6:
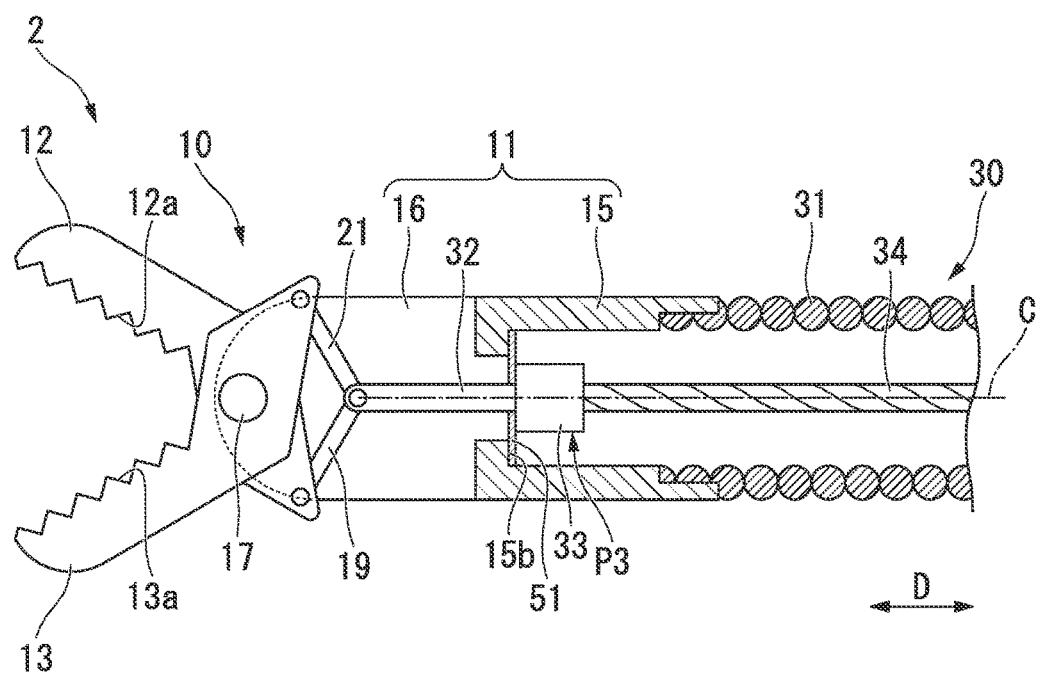
FIG. 6 is a cross-sectional view of the side surface on the distal end side in the third usage pattern of the gripping forceps.

If the slider 42 is further pushed, the stopper 33 further moves to the distal end side, as shown in FIG. 6. Accordingly, the plate spring 51 is elastically compressed in the longitudinal direction D by the stopper 33 and the support surface 15b, the plate spring 51 is further bent and approaches a flat shape, and the opening angle of the anti-slip surfaces 12a and 13a becomes large.

If the stopper 33 moves to the distal end side and reaches the compression position P3 until the stopper deforms the plate spring into a flat shape, the stopper 33 cannot be moved to the distal end side any further. The anti-slip surfaces 12a and 13a in this case are brought into the fully open state where the opening angle is the largest, and the gripping forceps 2 are brought into the third usage pattern.

As described above, according to the gripping forceps 2 of the present embodiment, the forceps members 12 and 13 can be easily adjusted into the half-open state where the opening angle of the anti-slip surfaces 12a and 13a is made to have a constant value.

Moreover, since the elastic member is the plate spring 51, the length of the elastic member in the longitudinal direction D becomes shorter compared to a case where the coil spring 35 is used as in the first embodiment. Accordingly, the length of the gripping forceps 2 in the longitudinal direction D can be shortened.

In the third usage pattern of the gripping forceps 2, since the plate spring 51 is deformed until the plate spring is formed into a flat shape, the slider 42 cannot be further pushed. Accordingly, the surgeon can easily recognize that the anti-slip surfaces 12a and 13a are in the fully open state.

In the present embodiment, a portion of an edge portion of the plate spring 51 may be attached to the support surface 15b. Even if such a configuration is adopted, the plate spring 51 can be deformed into a flat shape by pushing the stopper 33 via the slider 42. Moreover, the position of the plate spring 51 with respect to the distal end cover member 11 can be stabilized.

Third Embodiment

Next, although a third embodiment of the present invention will be described referring to FIGS. 7 to 10, the same parts as the above embodiment will be designated by the same reference numerals and the description thereof will be omitted, and only different points will be described.

Figure 7:
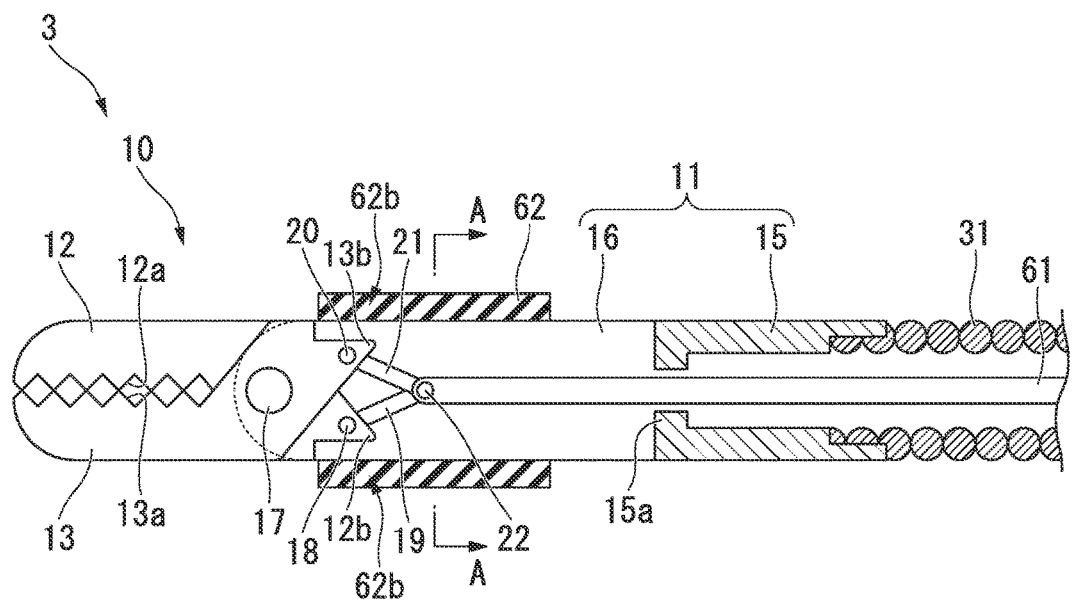
FIG. 7 is a cross-sectional view of the side surface on the distal end side in the first usage pattern of gripping forceps of a third embodiment of the present invention.
Figure 8:
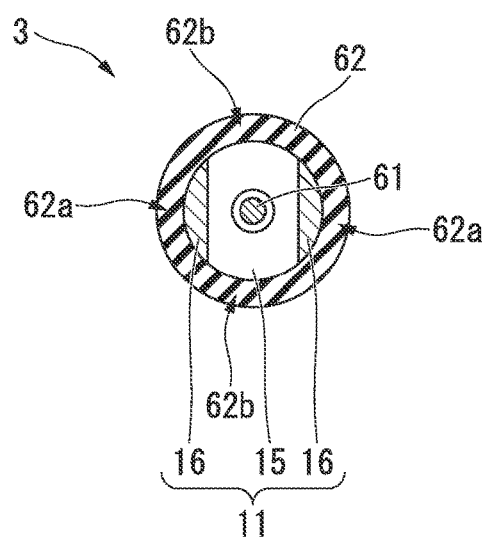
FIG. 8 is a cross-sectional view taken along cutting line A-A in FIG. 7.

As shown in FIGS. 7 and 8, gripping forceps 3 of the present embodiment include an operating wire (linear member) 61 and an elastic member 62, instead of the wire connector 32, the stopper 33, the operating wire 34, and the coil spring 35 of the gripping forceps 1 of the first embodiment.

The operating wire 61 is inserted through the cylindrical part 15 and the sheath 31 in a state where a distal end thereof is connected to the common rotation shaft 22, and a proximal end of the operating wire 61 is attached to the slider 42.

The elastic member 62 is formed in a cylindrical shape from materials having elasticity, such as rubber. The internal diameter of the elastic member 62 is set to be equal to or slightly smaller than the external diameter (an outer shape of the pair of covers 16 in their entirety in a direction where the pair of covers 16 are arranged side by side) of the covers 16. When the elastic member 62 is externally fitted to the pair of covers 16, contact portions 62a (refer to FIG. 8) that come into contact with the covers 16 apply compressive force on the outer peripheral surfaces of the covers 16 and are thereby supported by the pair of covers 16. Non-contact portions 62b of the elastic member 62 that do not come into contact with the covers 16 are in the natural state where no external forces other than gravity.

In the present embodiment, proximal ends of the forceps members 12 and 13 are locking portions 12b and 13b.

In the gripping forceps 3 configured in this way, as shown in FIG. 7, in the first usage pattern in which the anti-slip surfaces 12a and 13a are brought into the closed state, the locking portions 12b and 13b are arranged in a conduit of the elastic member 62, and are arranged at separated positions where the locking portions are separated from an inner peripheral surface of the elastic member 62.

Figure 9:
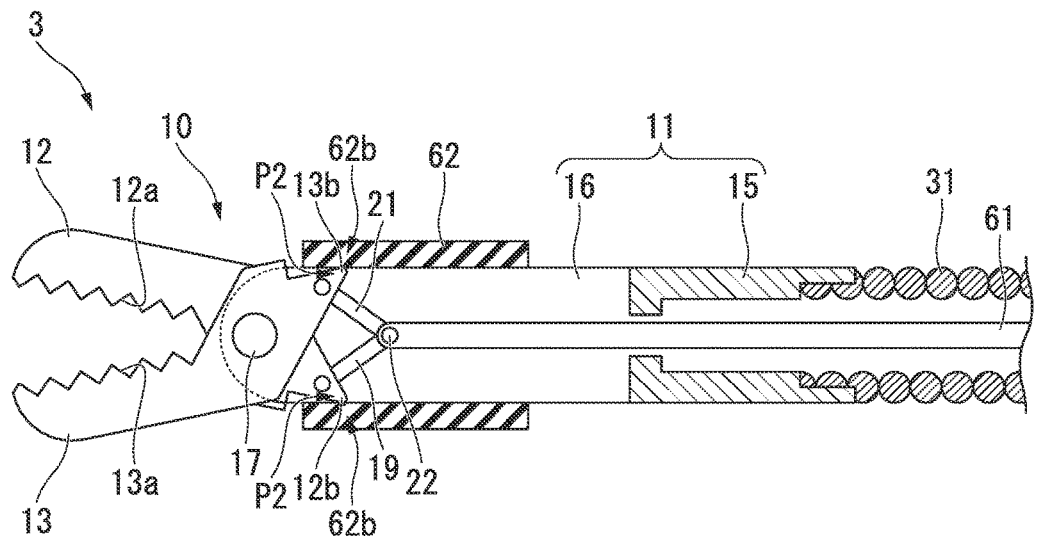
FIG. 9 is a cross-sectional view of the side surface on the distal end side in the second usage pattern of the gripping forceps.

Then, by pushing the slider 42, as shown in FIG. 9, the locking portions 12b and 13b move radially outward, and move to the contact position P2 where the locking portions come into contact with the non-contact portion 62b of the elastic member 62 in a natural state. Since the positions of the non-contact portion 62b in the natural state become constant with respect to the distal end cover member 11, the opening angle of the anti-slip surfaces 12a and 13a brought into the half-open state also has a constant value.

Figure 10:
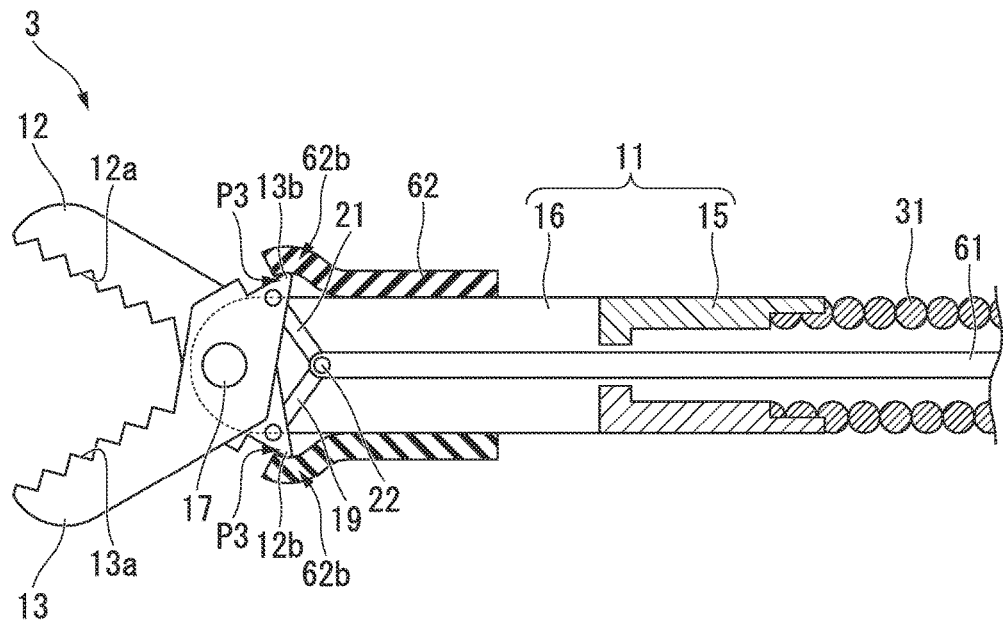
FIG. 10 is a cross-sectional view of the side surface on the distal end side in the third usage pattern of the gripping forceps.

If the slider 42 is further pushed, as shown in FIG. 10, the locking portions 12b and 13b further move radially outward, and move to a compression position P3 where the non-contact portion 62b is deformed radially outward.

In this case, since the common rotation shaft 22 moves to the distal end side together with the operating wire 61, the anti-slip surfaces 12a and 13a are brought into the fully open state where the opening angle is the largest, and the gripping forceps 3 are brought into the third usage pattern.

As described above, according to the gripping forceps 3 of the present embodiment, the forceps members 12 and 13 can be easily adjusted to the half-open state.

Since the proximal ends of the forceps members 12 and 13 are the locking portions 12b and 13b, the elastic member 62 to be deformed by the locking portions 12b and 13b can be kept away from the anti-slip surfaces 12a and 13a provided on the distal end side of the forceps members 12 and 13. Accordingly, when the anti-slip surfaces 12a and 13a are opened, the elastic member 62 can be prevented from becoming a hindrance.

In the present embodiment, the locking portions 12b and 13b are respectively provided at the proximal ends of the forceps members 12 and 13. However, a locking portion may be provided on one of the forceps members 12 and 13, or may be provided at an intermediate portion between the forceps members 12 and 13 in the extending direction.

Additionally, although the elastic member 62 is formed into the cylindrical shape, the cross-sectional shape of the elastic member in a plane orthogonal to the longitudinal direction D may be an elliptical shape, a polygonal shape, or the like.

Fourth Embodiment

Next, although a fourth embodiment of the present invention will be described referring to FIGS. 11 to 13, the same parts as the above embodiment will be designated by the same reference numerals and the description thereof will be omitted, and only different points will be described.

Figure 11:
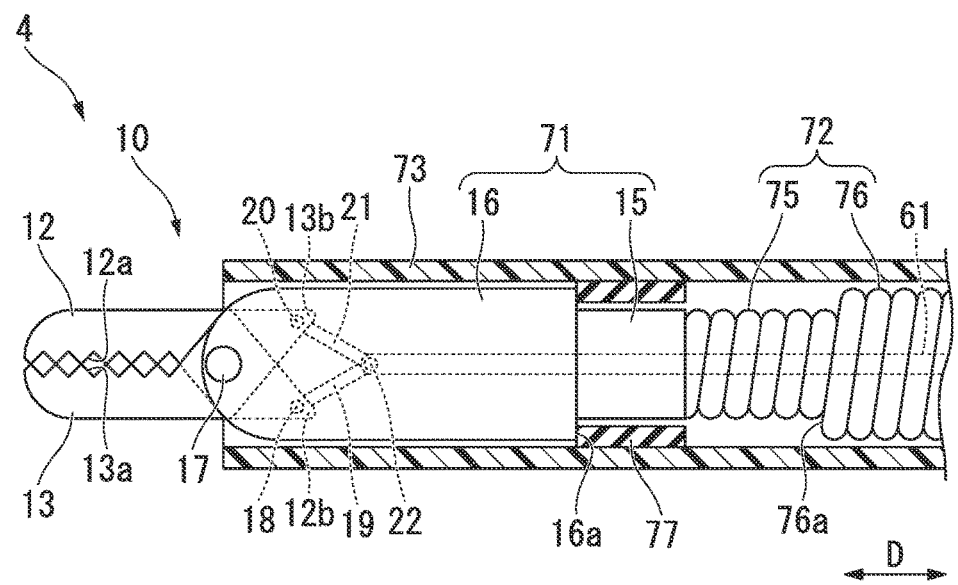
FIG. 11 is a cross-sectional view of the side surface on the distal end side in the first usage pattern of gripping forceps of a fourth embodiment of the present invention.
Figure 12:
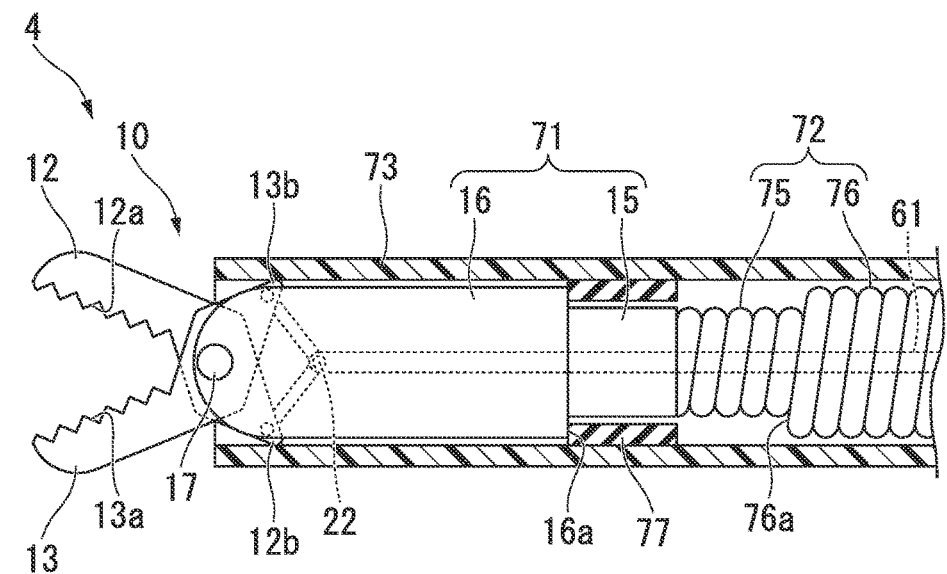
FIG. 12 is a cross-sectional view of the side surface on the distal end side in the second usage pattern of the gripping forceps.

As shown in FIG. 11, gripping forceps 4 of the present embodiment includes a distal end cover member 71, a sheath 72, and a covering tube 73, instead of the distal end cover member 11, the sheath 31, and the elastic member 62 of the gripping forceps 3 of the third embodiment.

In the distal end cover member 71, the diameters of the covers 16 are enlarged from the cylindrical part 15, and a stepped portion 16a is formed at a connecting portion between the covers 16 and the cylindrical part 15.

A sheath 72 has a configuration in which a distal end-side sheath 75 provided on the distal end side and a proximal-end-side sheath 76 provided on the proximal end side are connected together by welding or the like.

The external diameter of the distal end-side sheath 75 is set to be substantially equal to the external diameter of the cylindrical part 15, and the external diameter of the proximal-end-side sheath 76 is set to be substantially equal to the external diameter of the covers 16. A stepped portion 76a is formed at a connecting portion between the distal end-side sheath 75 and the proximal-end-side sheath 76.

While the covering tube 73 is formed from materials having flexibility, such as fluororesin, and the covering tube is formed from materials that are not easily deformed by pressing the locking portions 12b and 13b thereagainst. A cylindrical stopper member 77 is attached to an inner peripheral surface of the covering tube 73. The internal diameter of the stopper member 77 is set to be slightly greater than the external diameters of the cylindrical part 15 and the distal end-side sheath 75, and is set to be smaller than the external diameters of the covers 16 and the proximal-end-side sheath 76. As a material that forms the stopper member 77, resin, metal, or the like is preferably used.

The distal end cover member 71 and the sheath 72 are inserted through the covering tube 73, and the stopper member 77 is arranged between the stepped portion 16a of the distal end cover member 71 and the stepped portion 76a of the sheath 72 in the longitudinal direction D.

The gripping forceps 4 configured in this way are brought into the first usage pattern in which the anti-slip surfaces 12a and 13a are brought into the closed state by pulling back the slider 42 and by pushing the covering tube 73 with respect to the sheath 72 and locking the stopper member 77 to the stepped portion 16a of the distal end cover member 71. In this case, a distal end of the covering tube 73 is set so as to be arranged closer to the distal end side than the locking portions 12b and 13b in the longitudinal direction D. In the first usage pattern of the gripping forceps 4, the locking portions 12b and 13b are arranged at a position where the locking portions are separated from the inner peripheral surface of the covering tube 73.

The slider 42 is pushed from this first usage pattern, with the position of the covering tube 73 with respect to the sheath 72 being held. Accordingly, as shown in FIG. 12, the common rotation shaft 22 moves to the distal end side together with the operating wire 61, the opening angle of the anti-slip surfaces 12a and 13a becomes large, the locking portions 12b and 13b abut against the inner peripheral surface of the covering tube 73, and the locking portions 12b and 13b cannot be moved radially outward. The anti-slip surfaces 12a and 13a in this case are brought into the half-open state, and the gripping forceps 4 are brought into the second usage pattern.

Figure 13:
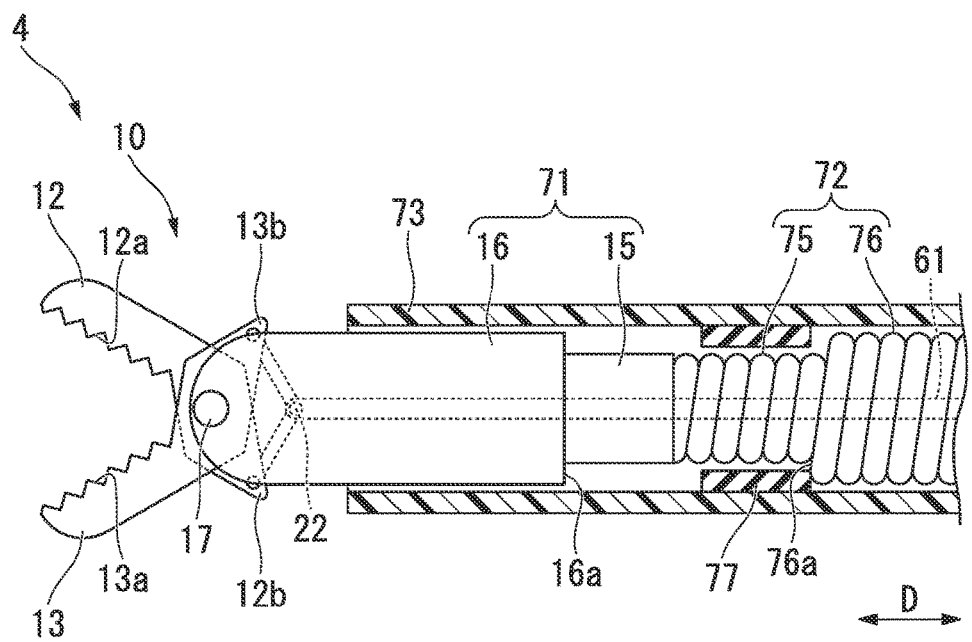
FIG. 13 is a cross-sectional view of the side surface on the distal end side in the third usage pattern of the gripping forceps.

As shown in FIG. 13, the distal end of the covering tube 73 is arranged closer to the proximal end side than the locking portions 12b and 13b in the longitudinal direction D by pulling back the covering tube 73 with respect to the sheath 72 and locking the stopper member 77 with respect to the stepped portion 76a of the sheath 72. If the slider 42 is further pushed with this state held, the locking portions 12b and 13b move radially outward and the opening angle of the anti-slip surfaces 12a and 13a becomes large, whereby the anti-slip surfaces 12a and 13a are brought into the fully open state and the gripping forceps 4 are brought into the third usage pattern.

As described above, according to the gripping forceps 4 of the present embodiment, the same effects as the gripping forceps 3 of the third embodiment can be exhibited.

Although the first to fourth embodiments of the present invention have been described above in detail with reference to the drawings, specific configuration is not limited to the embodiments, and changes of the configuration are also included without departing from the scope of the present invention. Moreover, it is obvious that the respective configurations shown in the respective embodiments may be appropriately combined and used.

The present invention is not limited only by the above description, but by the appended claims.

For example, in the first embodiment and the fourth embodiment, both of the forceps members 12 and 13 rotate around the rotation shaft 17. However, a configuration may be adopted in which one forceps member is fixed to the distal end cover member, and only the other forceps member rotates around the rotation shaft 17.

Additionally, the endoscope treatment tools are the gripping forceps in the first embodiment to the fourth embodiment. However, the endoscope treatment tools may be bipolar forceps for incision, suture devices, or the like without being limited to the gripping forceps.

INDUSTRIAL APPLICABILITY

According to the endoscope treatment tools of the above respective embodiments, a pair of forceps members can be easily adjusted to the half-open state where the opening angle has a constant value.

REFERENCE SIGNS LIST 1, 2, 3, 4: GRIPPING FORCEPS (ENDOSCOPE TREATMENT TOOL)
11, 71: DISTAL END COVER MEMBER (SUPPORT PART)
12, 13: FORCEPS MEMBER
12a, 13a: ANTI-SLIP SURFACE (OPPOSED SURFACE)
12b, 13b: LOCKING PORTION
15b: SUPPORT SURFACE
17: ROTATION SHAFT
31, 72: SHEATH
33: STOPPER (LOCKING PORTION)
35: COIL SPRING (ELASTIC MEMBER)
35a: ELEMENT WIRE
51: PLATE SPRING (ELASTIC MEMBER)
51a: THROUGH-HOLE
P2: CONTACT POSITION

The invention claimed is:
1. An endoscope treatment tool comprising:
a sheath;
a support part attached to a distal end portion of the sheath;
forceps members arranged in front of the sheath, supported so as to be relatively rotatable around a rotation shaft provided at the support part, and having a pair of opposed surfaces;
a linear member inserted through the sheath so as to be capable of advancing into and retracting from the sheath, bringing the opposed surfaces closer to each other at a position closer to a distal end side than the rotation shaft as the linear member is distanced from the rotation shaft, and separating the opposed surfaces from each other as the linear member approaches the rotation shaft;
an elastic member supported by the linear member or the support part, and the elastic member being configured to elastically deform in a longitudinal direction of the sheath; and
a locking portion provided on the linear member or the forceps members, wherein:
the locking portion does not contact the elastic member in a natural state when the linear member moves so as to be separated from the rotation shaft and the pair of the opposed surfaces abut against each other, the locking portion moves to a contact position where the locking portion comes into contact with the elastic member in the natural state when the linear member moves so as to approach the rotation shaft and the pair of the opposed surfaces are separated from each other, as the locking portion is further moved such that the locking portion moved to the contact position approaches the rotation shaft, the elastic member is elastically deformed, and the pair of opposed surfaces are further separated from each other than when the locking portion is located at the contact position, the elastic member is a coil spring in which an element wire is spirally wound and the element wires adjacent to each other are separated from each other in an axis direction of the spiral in the natural state, the coil spring is supported such that the linear member is inserted through the coil spring substantially parallel to the axis direction of the spiral, the locking portion is provided closer to a proximal end side of the linear member than the coil spring, the support part has a support surface that support the coil spring at a position closer to the distal end side than the coil spring, and the coil spring is compressed in a longitudinal direction of the sheath by the locking portion and the support surface when the linear member is moved so as to approach the rotation shaft.

2. The endoscope treatment tool according to claim claim 1, wherein the linear member is movable so as to approach the rotation shaft up to a position where the coil spring is elastically compressed and the element wires adjacent to each other in the axis direction abut against each other.

* * * * *